United States Patent [19]

Hogg, deceased

[11] Patent Number: 4,730,155

[45] Date of Patent: Mar. 8, 1988

[54] SAMPLING VALVE INCLUDING SAMPLE EJECTION MEANS

[75] Inventor: Walter R. Hogg, deceased, late of Miami, Fla., by Shirley J. Hogg, legal representative

[73] Assignee: Coulter Electronics, Inc., Hialeah, Fla.

[21] Appl. No.: 861,837

[22] Filed: May 12, 1986

[51] Int. Cl.$^4$ ............................................. G01N 27/07
[52] U.S. Cl. .................................. 324/71.1; 324/71.4
[58] Field of Search ...................... 324/71.1, 438, 439, 324/450, 71.4; 222/216, 217; 73/864.81, 864.83; 356/244, 246

[56] References Cited

U.S. PATENT DOCUMENTS

| | | | |
|---|---|---|---|
| 3,939,409 | 2/1976 | Hogg | 324/71.1 |
| 3,958,177 | 5/1976 | Reeves et al. | 324/71.1 |
| 4,471,297 | 9/1984 | Berg | 324/71.1 |

Primary Examiner—Gerard R. Strecker
Assistant Examiner—Robert W. Mueller
Attorney, Agent, or Firm—Sidney N. Fox; Gerald R. Hibnick

[57] ABSTRACT

A slide motion sampling valve for use with a particle study device and carrying an expansive type microsyringe having a minimum trapped volume. The sampling valve is formed of a slidably movable member carrying a trapping volume, an expansive element and ejection port in the form of a fine aperture, and a stationary element sealingly engaged with said movable member and carrying an opening leading to the entrance of the sheath flow arrangement. The valve operates between a conditon where the ejection port and the opening are aligned and a condition where communication to the entrance is blocked whereby to isolate the trapping volume from said entrance except during ejection of the predetermined amount. One embodiment described employs a linear sliding motion while another embodiment employs a rotating sliding motion.

24 Claims, 4 Drawing Figures

SAMPLING VALVE INCLUDING SAMPLE EJECTION MEANS

CROSS-REFERENCE TO RELATED PATENTS

This invention relates to and is an improvement over the subject matter of U.S. Pat. Nos. 3,890,569 and 3,939,409 respectively granted June 17, 1975 and Feb. 17, 1976, both owned by the Assignee hereof; the specification of both of these identified patents being incorporated by reference herein as supplying background and explanatory disclosure as an aid in the understanding and appreciation of the invention herein.

BACKGROUND OF THE INVENTION

This invention relates generally to particle study device and more particularly provides an improved device for delivering a predetermined amount of particulate matter into a flowing carrier sheath liquid leading to a sensing zone.

Ejecting mechanisms have been disclosed in the referenced United States patents which mechanisms operate to eject a predetermined amount of particulate matter into an electrolytic diluent leading to the sensing zone within a particle study device, preferably of the Coulter type. These ejecting mechanisms include those which had to be loaded manually with particulate matter and those which were coupled automatically to direct a predetermined amount of trapped particulate matter to a flowing sheath of diluent functioning as a carrier. The flowing sheath leads the particulate matter to a sensing zone when said mechanism is coupled thereto.

As known, where a flow sheath of carrier liquid is generated, the individual particles follow a straight line through the center of the path traveled by the sheath, the particles and the sheath traveling in distinct streams. While not uniformly spaced, the particles do travel along a straight line in an ordered fashion.

Such ejecting devices include a fine ejecting aperture of microscopic proportions leading from a reservoir carrying a volume of trapped sample to a sheath flow device. It would be desirable to seal off the said aperture during the trapping of said sample within the reservoir. If one desired to enlarge the ejecting aperture to slightly greater than microscopic proportion, undesired mixing could be a problem. Likewise the prevention of such undesired mixing has depended to a considerable extent upon the maintenance of a desired surface tension during the trapping phase. This is not always feasible. Further, when the ejecting assembly is permanently mounted to the flow sheath arrangement, sealing becomes a considerable problem which requires expensive precision in the fabrication of the shear valve action valves utilized therewith.

Thus it would be highly desirable to provide against such undesired mixing in the transport of the sample and liquids through the systems such as typified by the referenced patents.

SUMMARY OF THE INVENTION

A particle study device is provided wherein particulate matter enclosed in a flowing sheath carrier liquid is passed through a sensing zone for counting and sizing. The particle study device includes a sample metering mechanism comprising a sampling valve including a sealingly engaged stationary portion and a slidably movable portion, the latter normally carrying a reservoir including an expansive device and a fine aperture, the stationary portion including an opening arranged offset from the aperture in one condition of the valve and aligned therewith in a second condition of the valve. Means defining a flow sheath arrangement and containing a sensing zone are coupled sealingly to said stationary element with the aforementioned opening aligned with an entrance leading to the sensing zone. Suitable conduit means are provided for defining a flow path for particulate matter into the reservoir and means are coupled to the flow sheath for distributing the sheath defining liquid thereto for entraining the ejected sample just prior to the passage thereof through the sensing zone. A suitable drain is provided downstream of the sensing zone for directing the flow subsequent to passage through said sensing zone.

DESCRIPTION OF PREFERRED EMBODIMENTS

Figure 1:
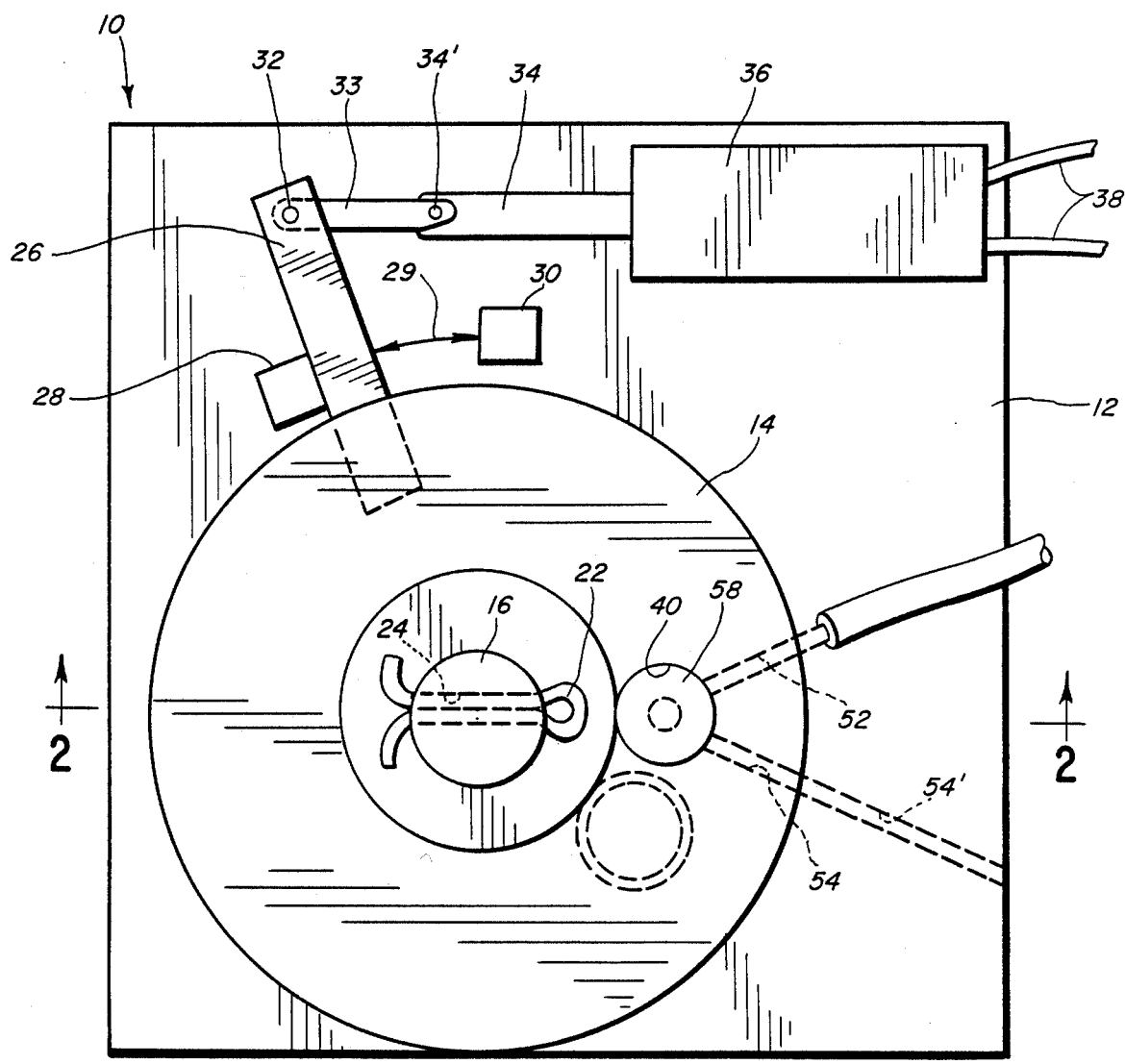
FIG. 1 is a plan view of the sample metering device according to the invention and illustrated in the loading condition thereof.
Figure 2:
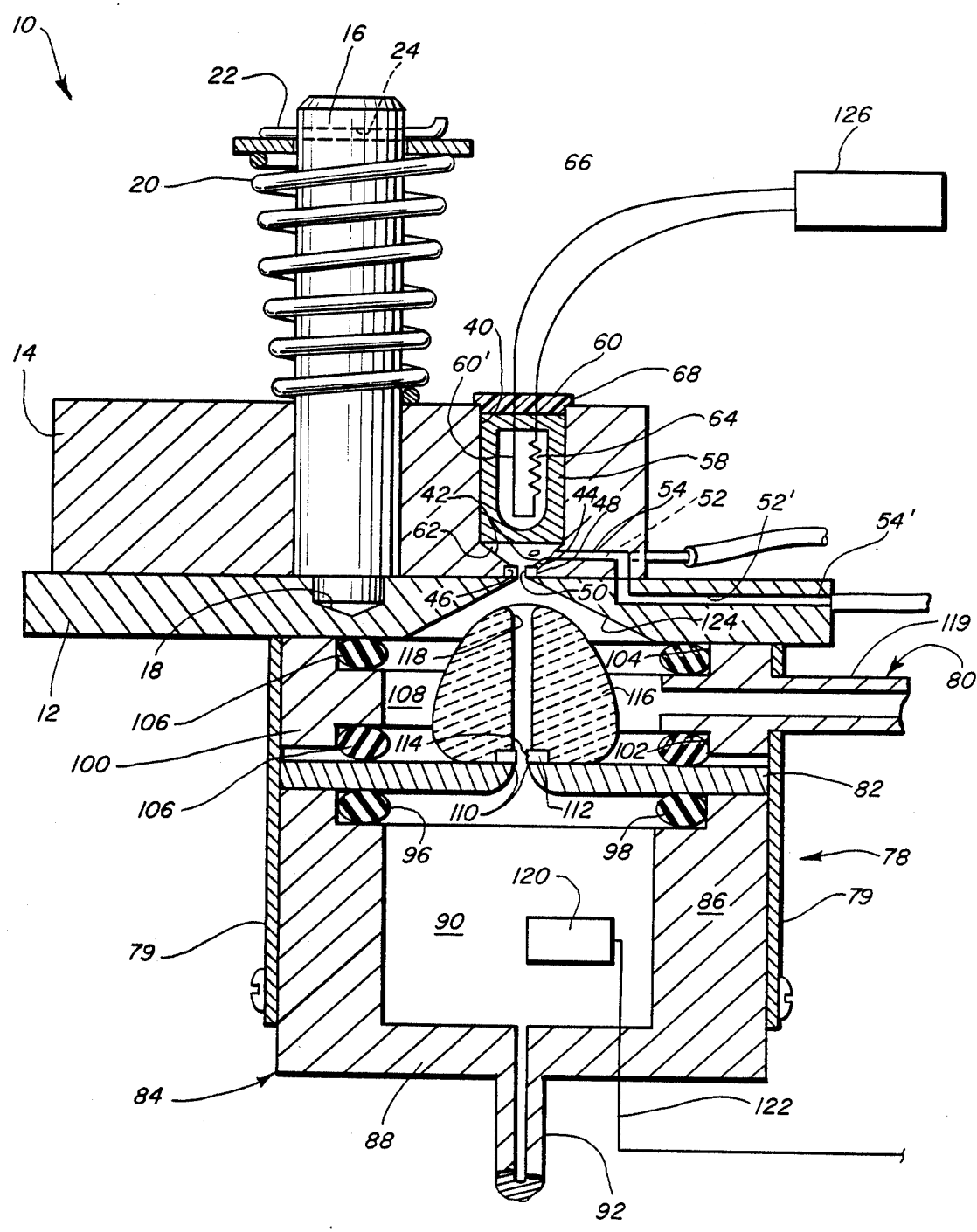
FIG. 2 is a sectional view of the sample metering device and the sensing zone arrangement of the invention, but illustrated in the ejecting or delivering condition of the metering device.

Referring to FIGS. 1 and 2, a sample metering device according to this invention is designated generally by reference character 10 and includes a stationary plate 12 and a rotatable slidably movable member 14 sealingly engaged with the plate 12. The assembly of members 12 and 14 is maintained by spring biased keeper post 16 seated in beveled well 18 formed in said member 12. The spring 20 is retained by cotter pin 22 engaged through suitable passage 24 formed in the upper end of the post 16.

Lever or handle 26 is secured to the member 14 for rotary translatory motion along a path between a pair of spaced stops 28 and 30 in the direction of arrows 29. The free end of handle 26 carries a pin 32 to which is secured, pivotally, link 33 attached to pin 34' of a reciprocable arm 34 of actuator member 36. The actuator member 36 may be electrically powered such as a solenoid device or may be a hydraulically or fluid pressure operated device. Suitable connections 38 lead to a power source (not shown) such as a source of fluid pressure or vacuum, or an electric current, etc.

A generally cylindrical cavity 40 is formed in member 14, the axis thereof being parallel with the center axis of member 14. Cavity 40 has a conical floor 42 leading to an aperture 44 of fine proportion, preferably microscopic in diameter. Aperture 44 may lead from the floor 42 directly to the undersurface of member 14 or may open to a shallow recess 46 in which insert 48 is tightly seated. In such instance, the insert 48 carries the precise, fine aperture 50 with aperture 44 being of larger diameter. When the insert 48 is installed, the aperture 50, which would constitute the ejecting port, is aligned with aperture 44.

Suitable angular passageways or bores 52,54 are formed in element 14 leading to the reservoir 62 and are coupled to passageways or bores 52' and 54' formed in the stationary member 12 and lead to a source of sample (not shown) together with bores 52,54 in one condition of the member 14 and being blocked from said source in the moved or other condition of said member 14. Together with said bores 52' and 54', bores 52,54 define a flow path to and through the reservoir 62 for receiving the sample to be studied using the apparatus of the herein invention.

An expansive element 60 comprising an elastic outer member 58, preferably of electrically and thermally insulating material surrounding a thermal expansion element 60' is seated within the cavity 40 above the conical floor 42 to define a reservoir chamber 62. Cover disc 68 is mounted over element 60 to secure same in said cavity. The chamber 62 has a minimal volume, just constituting the space between the conical floor 42 and the member 58. A resistor 64 is embedded in the expansion element 60 and lead wires 66 are secured to the terminals of the resistor 64, same passing through elastic outer member 58 coupling same to the electrical control circuitry 126. The wires 66 are drawn through a suitable rigid sealing compound plug.

The sample metering device 10 sealingly is coupled to the assembly 78 which includes an electrolyte flow assembly 80, an apertured plate 82 and a cylindrically shaped housing 84 formed of glass or other insulating material. Housing 84 has a cylindrical side wall 86 and a bottom wall 88 defining a chamber 90. Axial drain tube 92 is formed centrally through the bottom wall 88 and extends downwardly from the housing 84. The top edges of the side wall 86 carry annular grooves 96 for receiving O-rings 98 seated therein so as to provide a seal between the plate 82 and the housing 84.

The carrier liquid preferably utilized herein is an electrolyte and is introduced to the chamber 90 by an electrolyte flow assembly 80 including a hollow ring 100 formed primarily from stainless steel or other non-corrosive material. Annular grooves 102 and 104 are formed in the ring 100 for receipt therein of suitable O-rings 106 to effect a sealed coupling between the ring 100, the apertured plate 82 and plate 12.

The plate 82 divides chamber 90 and defines a chamber portion 108 above said plate and carries a minute central passage 110. An annular ring 116 formed of glass is positioned on and secured to the top surface of plate 82. Ring 116 is of conical configuration and has an entrance 118 under which is seated permanently a ruby or sapphire wafer 112 carrying precise fine aperture 114. The passage 110, aperture 114 and entrance 118 are coaxial. The apertures 50 and 114 are close together to reduce the length of the path to the sensing zone, said ring 116 being disposed within the chamber portion 108.

If the electrolyte flow ring assembly is formed of insulating material, an electrode is disposed within the chamber 108 and is connected to the detecting and analyzing circuitry (not shown) for monitoring the passage of said particulate material through the restricted orifice defined by said aperture 114. The ring 100 has an arm 119 which extends radially outward of the side wall 86 of housing 84. Since the ring 100 is formed of a conductive material such as stainless steel, the ring 100 functions as an electrode when suitably connected, and a second electrode 120 is disposed within the remaining chamber 90 below the plate 82. A conductor 122 connects the second electrode to the detecting and analyzing circuitry.

A counter-sunk passage 124 is formed in the member 12 and is located so that it is coaxial with the entrance to the aperture 114. The member 14 is translated between two conditions, one being when the aperture 50 is blocked by the imperforate section of the member 14 and the second being when said aperture 50 and passage 124 are coaxial and aligned.

The connecting wires 66 of element 60 are coupled to a control device 126. At the second condition, power is directed to resistor 64. The heat generated by energized resistor 64 causes the thermal expansion of element 58 to force a minute precise quantity of sample through said aperture 50 into the chamber 108 and to and through the sensing zone of the apparatus 10, which is the constricted area within the aperture 114 across which the current field is defined by the pair of electrodes 100 and 120.

The device 10 and assembly 78 are primed with carrier liquids, here electrolyte. When the predetermined amount of particulate sample is ejected via ejection port 50 and enters the chamber 108, the carrier liquid is allowed to flow into the chamber 108 from ring 100 and flows around annular ring 116 to the aperture 114 defining a sheath flow therethrough and provides a conductive current path between the pair of electrodes 100 and 120. In passing to and through the aperture 114, the ejected amount of particulate matter follows a path sheathed by the carrier liquid (electrolyte). The sample particles flow in seriatim through the aperture 114 along the central path therethrough causing a change in impedance between said electrodes 100 and 120 which is sensed by the particle analyzing circuitry (not shown) for counting the particles and analyzing the various characteristics of said particles.

As in the patented device of U.S. Pat. No. 3,939,409, the entire assembly including the housing 84, the flow sheath assembly and the plate 82 are maintained in assembly via clamps 79. When the ejection has been effected, the actuator device 36 is energized to translate the handle 26 back to its load condition.

Figure 3:
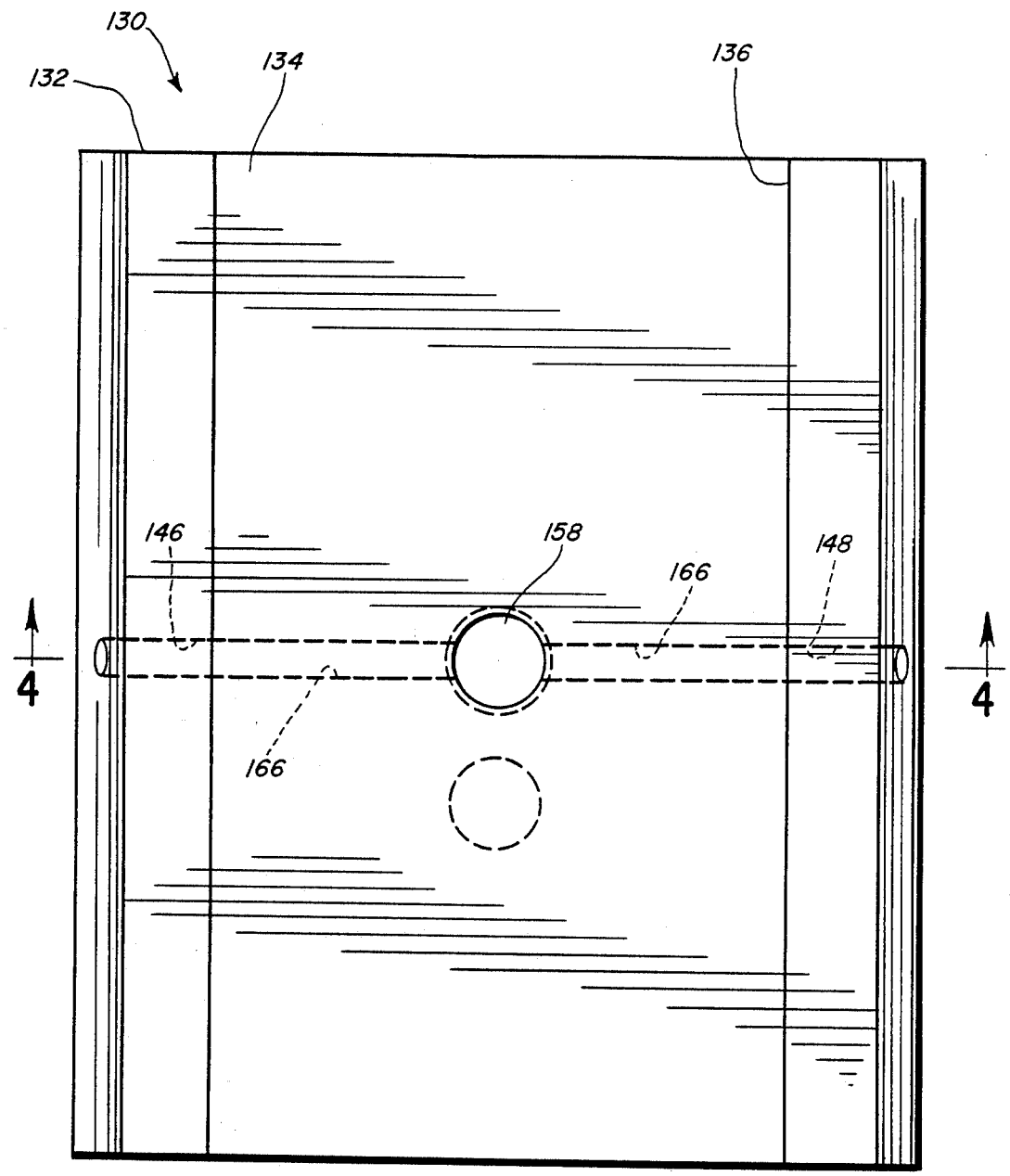
FIG. 3 is a plan view of a modified sample metering device according to the invention, shown in the loading condition.
Figure 4:
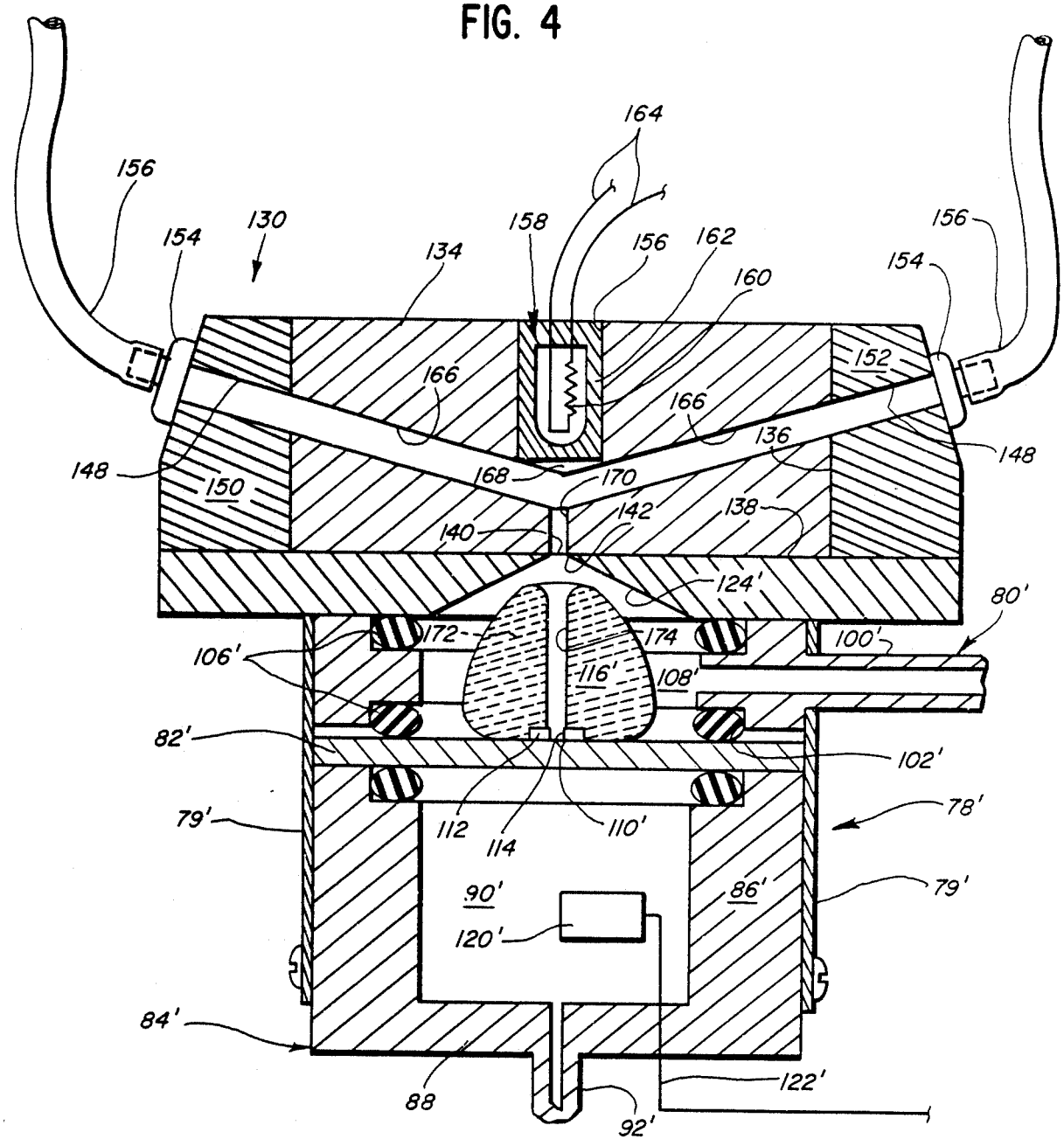
FIG. 4 is a sectional view of the sample metering device of FIG. 3 but shown in the ejecting or delivering condition of the metering device.

Referring now to FIGS. 3 and 4, the invention is illustrated in modified form wherein the rotary slidably translatable sample metering device 10 has been replaced by a linearly movable sample metering device 130.

The linearly movable device 130 comprises a generally rectangular body member 132 carrying a track 136 for accommodating a slide element 134 for limited movement. The floor 138 of track 136 carries a through passage 140 having a minimum diameter entrance 142 and flaring outwardly along its remaining wall area. A pair of angular cross bores 146 and 148 are formed through the side walls 150 and 152, each bore 146 and 148 having suitable fittings 154 for mounting suitable conduits or flexible tubing 156 coupled to a source of particulate matter and a dispositive location therefor.

The slide element 134 includes a generally cylindrical cavity 156 into which is disposed tightly an expansion element 158, including a resistor 160 encased in a resilient jacket 162 and electrical connectors 164 are brought out for connection to the appropriate circuitry (not shown). A pair of angular bores 166 are formed in slide element 134 and arranged angularly to converge in chamber 168 defined at the bottom end of expansion element 158. A fine aperture 170, preferably of microscopic dimension is formed at the juncture of said bores 166. The entrance 142 to passage 140 is located to be aligned with aperture 170 in one condition of the element 134 and blocked by the body of element 134 at other times. The bores 166 are angled to assure that the path through aperture 170 is as small as possible to facilitate drainage and minimize carry over.

The sample of particulate matter such as blood is drawn through the metering valve device 130 along the flow path defined by the bores 146, 166 and 148 through the chamber 168. The slide element is moved in a linear direction along track 136 trapping a volume of sample within the bores 166, particularly within the chamber 168; the aperture 170 aligned with the entrance 142, and the thermal expansion element 158 energized, causing, as heretofore described, the predetermined amount of sample to be ejected through said aperture 170.

The metering device 130 is coupled to the flow arrangement assembly described heretofore for transporting the particulate material to and through the sensing zone.

In the embodiment illustrated in FIGS. 3 and 4 a ring 172 has an annular configuration and has an axial channel 174. The plate 82 in this instance would carry the apertured wafer 112, which in turn carries scanning aperture 114. The flow sheath of carrier liquid travels the length of the channel 174 to reach the scanning aperture, carrying therealong the train of particulate matter of the sample. Elements common to the rotary embodiment of FIGS. 1 and 2 are indicated with primed reference numbers equivalent to those reference numbers employed in FIG. 2.

It should be understood that although the devices illustrated in the FIGS. 1 to 4 inclusive are shown in one orientation, the use of the devices is not limited to such orientation. The devices can be employed in substantially any orientation and in particular, the invention as embodied in the described embodiments, is not limited to gravity feed operation. Only minor, if any, changes and/or adjustments may be needed for use in different orientation from that illustrated. Suitable conduits may be provided through the housing wall 86 of assembly 78 for the purpose say of introducing electrolyte thereinto for aid in fully priming the system. Another conduit leading into chamber 90 can be employed for the purpose of removing any accumulated or accumulating bubbles, if any should develop. Further, the structure disclosed for providing the flow sheath of carrier liquid serve only as examples of the type of structures which may be employed and are not to be considered to be limiting of the possible flow sheath defining structures which may be constructed and employed in the environment of this invention.

Other variations are contemplated without departing from the spirit and scope of this invention as defined in the appended claims

What I claim is:

1. In a sample metering device for use in a particle study device wherein particulate matter is passed through a sensing zone including in combination, an input for receiving a sample of particulate matter, a drain for expelling the sample, an ejection port, means for trapping a volume of said particulate matter, ejecting means for ejecting a predetermined amount of said trapped volume through said ejection port and means for sealing off the trapping means, ejecting means and ejection port from the sensing zone and drain during trapping of said volume.

2. The device as claimed in claim 1 wherein said device includes a stationary element and a slidably movable element sealingly engaged therewith, said trapping means and ejecting means carried by said movable element, said trapping means including a reservoir, and thermal expansion means communicating directly with said reservoir and being operative in response to a control signal to expand and eject said amount of trapped sample through said ejecting port.

3. The device as claimed in claim 1 and a housing defining a chamber, a conduit coupled to said chamber and to said source of diluent for introducing carrier liquid to said chamber, said ejecting port and said chamber being in communication with said ejecting port and to said sensing zone, means defining a flow sheath of said carrier liquid for leading said ejected amount to said sensing zone.

4. The device as claimed in claim 3 and a wall in communication with said chamber, scanning aperture means formed in said wall for allowing the sheath flow and ejected amount therethrough, said wall defining a second chamber downstream of said aperture and electrode means in said chambers on opposite sides of said aperture means.

5. The structure as claimed in claim 4 wherein said conduit defines one electrode of said electrode means.

6. The structure as claimed in claim 1 wherein said sealing means comprise a thin plate carrying an opening and arranged between said ejection port and said chamber, said ejection port being blocked during the trapping condition of said metering means and aligned with said opening in communication with said chamber in the ejecting condition.

7. The structure as claimed in claim 2 and limit means defining the path of movement of said movable element.

8. The structure as claimed in claim 2 in which said movable element is linearly translatable.

9. The structure as claimed in claim 2 in which said movable element is slidably rotatable.

10. In a sample metering device capable of delivering a predetermined amount of particulate matter to a location and comprising slide valve means including a movable element arranged for limited slidable movement, means within said movable element defining a reservoir, means defining a flow path communicating to and from said reservoir for loading same from a source of particulate matter, said movable element being translatable for trapping a volume of said particulate matter within said reservoir, thermal expansion means carried by said movable element and communicating directly to said reservoir, fine aperture means formed in said movable element and communicating with said reservoir, passage means leading to said location, said thermal expansion means capable of being energized to expand for ejecting said predetermined amount from said reservoir the inprovement comprising blocking means interposed between said fine aperture means and said passage means for isolating said reservoir and fine aperture means from said passage means and said location at least during the loading of said reservoir and carrying a passageway, said blocking means arranged to permit communication between said fine aperture means and said passage means only during energization of said expansion means.

11. The structure as claimed in claim 10 in which said slide valve means includes a stationary element and said movable element is sealingly engaged therewith, said blocking means comprising said stationary element and said passageway being formed therein located offset from said aperture means during loading of said reservoir and alignable with said passage means, said movable element being slidable subsequent to loading of said reservoir to align said aperture means and passageway for ejection of said predetermined amount.

12. The structure as claimed in claim 10 in which said slide valve means includes a stationary element having an imperforate area and said elements are relatively movable between a first position isolating said reservoir from said passage means and establishing communication with said flow path for loading said reservoir, and a second position establishing communication to said passage means via said fine aperture means.

13. The valve as claimed in claim 12 wherein said elements are linearly translatable, one relative to the other.

14. The valve as claimed in claim 12 wherein said elements are rotatively translatable one relative to the other.

15. The valve as claimed in claim 13 and limit means defining the extent of relative movement of said elements.

16. The valve as claimed in claim 14 and limit means defining the extent of relative movement of said elements.

17. The valve as claimed in claim 10 and means coupling said valve means to a particle analyzing device including a chamber for receiving said ejected particulate matter, means for introducing electrolyte to said receiving chamber for defining a flow sheath to the sensing zone for carrying the ejected amount to the sensing zone assembly interposed in the flow path from said receiving chamber and means maintaining said valve means and analyzing device in coupled condition.

18. In a particle study device wherein particulate matter in a fluid suspension is passed through a sensing zone, sample metering means including a reservoir, means defining a flow path for leading a sample particulate matter to and from said reservoir, an ejection port communicating to said reservoir, thermal expansion means within said sample metering means positioned in direct communication with said reservoir and operative in response to a control signal to expand and thereby to eject a predetermined amount of particulate matter from said reservoir to and through said ejection port, means for receiving said ejected amount and leading same to the sensing zone; the improvement comprising means for selectively isolating the reservoir from the receiving means and sensing zone except during ejection of the predetermined amount.

19. The structure as claimed in claim 18 in which said sample metering means comprise a slide valve having a slidable element seated sealingly engaged with a stationary element, said movable element carrying said reservoir and ejection port and said isolating means comprise a passage formed in said stationary member and located misaligned with said ejection port during loading condition of the reservoir and aligned with said ejection port during delivery of said ejected amount.

20. The structure as claimed in claim 19 in which said expansion means is carried by said slidable element.

21. The structure as claimed in claim 18 including coupling means coupled to said sample metering means and to a source of carrier liquid and to said sensing zone for defining a flow sheath for leading said ejected amount to and through the aperture.

22. In a particle study device wherein a particulate matter in liquid suspension is passed through a sensing zone, sample metering valve means including a stationary element and a slidably movable element sealingly engaged therewith for limited relative movement therewith, a reservoir defined within said movement element and means defining a flow path through said elements and communicating with said reservoir for leading said particulate matter from a source to said reservoir in one condition of said elements whereby a predetermined amount of said particulate matter is trapped within said reservoir, selectively operable thermal expansion means carried by said movable element and communicating directly with the trapped content of said reservoir, an ejection port formed in said movable member and communicating to the reservoir, means coupling said sample metering valve means with a sensing zone and including a receiving chamber having an entrance for receiving said predetermined amount and for introducing diluent from a source thereof to said chamber defining a flow sheath leading said predetermined amount to and through the sensing zone; the improvement comprising slidable means selectively for sealing off the ejection port from the entrance during said trapping of said sample and thereafter establishing communication between the ejection port and the entrance.

23. The device as claimed in claim 22 wherein said means for sealing off the ejection port and the entrance comprising a slide member carrying the ejection port, said slide member being linearly slidably movable sealingly relative to the stationary element.

24. The device as claimed in claim 22 in which means for sealing off the ejection port and the entrance comprising a slide member carrying the ejection port and said slide member rotatably is slidable sealingly relative to the stationary element, said slide member carrying the reservoir and the expansion means.

* * * * *

UNITED STATES PATENT AND TRADEMARK OFFICE
CERTIFICATE OF CORRECTION

PATENT NO. : 4,730,155

DATED : March 8, 1988

INVENTOR(S) : Walter R. Hogg, deceased

It is certified that error appears in the above—identified patent and that said Letters Patent is hereby corrected as shown below:

Column 6, line 55, after "reservoir" insert --;--;
Column 6, line 56, change "inprovement" to --improvement--;
Column 7, line 37, after "in" delete --a--;
Column 8, line 20, change "movement" to --movable--.

Signed and Sealed this

Ninth Day of July, 1991

Attest:

HARRY F. MANBECK, JR.

*Attesting Officer*    *Commissioner of Patents and Trademarks*